United States Patent [19]

Okamoto et al.

[11] Patent Number: 4,902,099

[45] Date of Patent: Feb. 20, 1990

[54] TRACE ELEMENT SPECTROMETRY WITH PLASMA SOURCE

[75] Inventors: Yukio Okamoto, Sagamihara; Makoto Yasuda, Kodaira; Seiichi Murayama, Kokubunji; Masataka Koga, Katsuta, all of Japan

[73] Assignee: Hitachi, Ltd., Tokyo, Japan

[21] Appl. No.: 285,754

[22] Filed: Dec. 16, 1988

[30] Foreign Application Priority Data

Dec. 18, 1987 [JP] Japan .................. 62-318813

[51] Int. Cl.$^4$ .......................................... G01N 21/73
[52] U.S. Cl. .................. 356/316; 219/121.36; 219/121.48; 250/281; 250/288; 315/111.21
[58] Field of Search .................. 356/316; 315/111.21; 219/121.36, 121.48; 250/281, 288

[56] References Cited

PUBLICATIONS

Beenakker et al, *Spectrochimica Acta*, vol. 33B, No. 7, 1978, pp. 373–381.
Estes et al, *Analytical Chemistry*, vol. 53, No. 9, Aug. 1981, pp. 1336–1340.
Goode et al, *Applied Spectroscopy*, vol. 38, No. 6, Nov./Dec. 1984, pp. 755–763.
Leis et al, *Spectrochimica Acta*, vol. 39B, No. 9–11, 1984, pp. 1459–1463.
Boumans et al, *Philips Tech Review*, vol. 33, No. 2, 1973, pp. 50–59.
Deutsch et al, *Applied Spectroscopy*, vol. 39, No. 2, 1985, pp. 214–222.
Abdallah et al, *Spectrochimca Acta*, vol. 37B, No. 7, 1982, pp. 583–592.
Zander et al, *Analytical Chemistry*, vol. 50, No. 9, Aug. 1978, pp. 1257–1260.

*Primary Examiner*—F. L. Evans
*Attorney, Agent, or Firm*—Antonelli, Terry & Wands

[57] ABSTRACT

A plasma trace element spectrometer comprises a microwave generator for generating microwave power, a microwave feeder for guiding and transforming the generated microwave power into microwave power of $TE_{01}$ mode and supplying the microwave power of $TE_{01}$ mode, a plasma producer having, at one end, an introduction port for a carrier gas and a sample and at the other end an opening and being cooperative with the supplied microwave power of $TE_{01}$ mode to produce plasma of the carrier gas and sample introduced through the introduction port, and a spectrometer for analyzing constituent elements of the sample by measuring the produced plasma by way of the opening.

6 Claims, 7 Drawing Sheets

TRACE ELEMENT SPECTROMETRY WITH PLASMA SOURCE

BACKGROUND OF THE INVENTION

This invention relates to a trace element spectrometer with plasma source (simply referred to as a plasma trace element spectrometer hereinafter) such as plasma source mass spectrometer or plasma emission spectrometer used for quantitative analysis of trace elements in the field of biology and the like, and more particularly to a means of plasma production using microwave power suitable for improving excitation efficiency for samples in this type of spectrometer.

Conventionally, there have been available two types of plasma production means in the plasma trace element spectrometer, one type using RF power at 27 MHz (for example, Philips Tech. Rev., Vol. 33, No. 2 (1973), pp. 50–59: literature 1) and the other using microwave power at 2.45 GHz. The apparatus utilizing microwave power is further classified into two types: one uses a microwave cavity with $TM_{010}$ mode (for example, Applied Spectroscopy, Vol. 39, No. 2 (1985), pp. 214–222: literature 2) and the other is based on a surface wave excitation with capacitive coupling method and called "Surfatron" (for example, Spectrochimica Acta, Vol. 37B, No. 7 (1982), pp. 583–592: literature 3).

Of the above prior arts, the RF excitation method disclosed in literature 1 can provide a radial distribution of plasma parameters (such as temperature and density), which is ideal for the trace element spectrometer but it leads to disadvantages of large-sized and expensive apparatus, low ionization efficiency and complexity in adjustment. On the contrary, the microwave excitation method of literatures 2 and 3 can eliminate the problems encountered in literature 1 but suffers from disadvantages of degraded characteristics of radial distribution of the plasma parameters, low introduction efficiency for samples non-uniformity in heating and ionization of the sample particles and low measurement sensitivity.

SUMMARY OF THE INVENTION

An object of this invention is to provide a plasma trace element spectrometer with high performance which can eliminate various problems faced by the prior arts.

According to the invention, to accomplish the above object, microwave power for plasma production is supplied under an electric field distribution of $TE_{01}$ mode.

The electric field distribution of $TE_{01}$ mode is effective to produce doughnut type plasma which resembles RF inductively coupled plasma of literature 1. With this type of plasma, sample particles can be introduced to the central part of the plasma easily and efficiently and besides the radial distribution of the plasma parameters can be optimized for analysis or spectrometer to achieve improvements in various characteristics including uniformed ionization and improved detection sensitivity.

Further, since the microwave power can be utilized more efficiently in the $TE_{01}$ mode, the spectrometer can be reduced in size and power consumption and simplified for adjustment.

DESCRIPTION OF THE PREFERRED EMBODIMENTS

Figure 1:
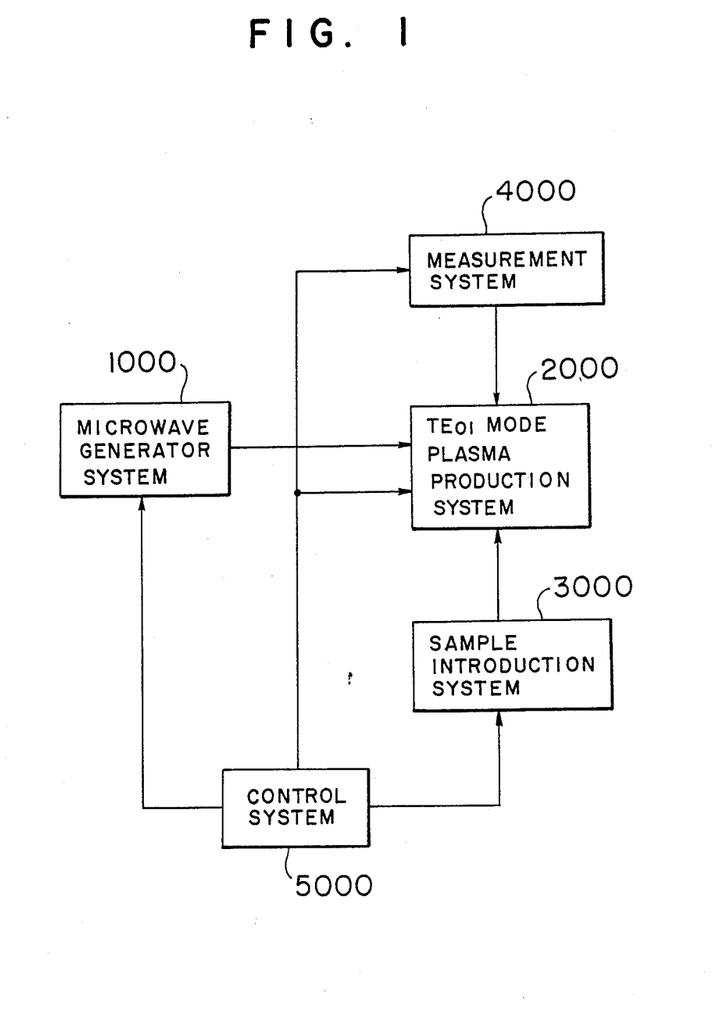
FIG. 1 is a schematic block diagram illustrating the fundamental construction of a spectrometer according to an embodiment of the invention.

Referring now to FIG. 1, there is illustrated, in schematic block diagram, a plasma trace element spectrometer according to an embodiment of the invention. This apparatus comprises a microwave generator system 1000, a $TE_{01}$ mode plasma production system 2000, a sample introduction system 3000, a measurement system 4000 and a control system 5000. The microwave generator system 1000 includes a microwave generator such as magnetron or gyrotron, a high voltage power supply, a microwave power meter and a tuner, the $TE_{01}$ mode plasma production system 2000 includes a microwave antenna for mode generation and a discharge tube, the measurement system 4000 includes a spectrometer, a mass analyzer and a display device, and the control system 5000 includes a microcomputer for controlling each of the above systems.

The $TE_{01}$ mode plasma production system 2000 is essential to the invention and its antenna structure for $TE_{01}$ mode generation will be described below with reference to FIGS. 2A, 2B and FIGS. 3A, 3B.

Figure 2A:
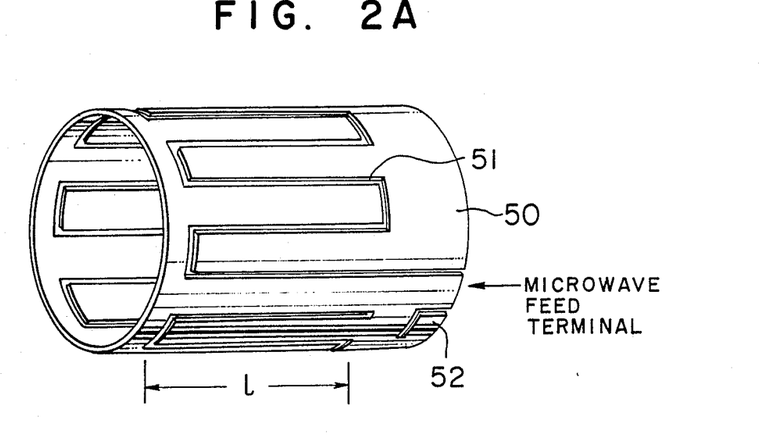
FIGS. 2A and 2B are perspective views illustrating different examples of antenna according to the invention used to generate an electric field distribution as shown in FIGS. 3A and 3B.
Figure 2B:
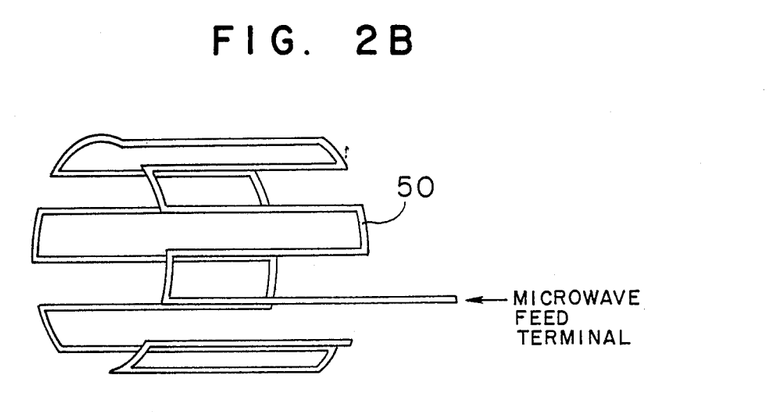

Illustrated in FIGS. 2A and 2B are specific examples of microwave antenna 50 according to the invention adapted to generate an electric field distribution of $TE_{01}$ mode. In FIG. 2A, a plurality of slots 51 are formed in a cylindrical conductor made of, for example, copper. Each slot 51 has a length l which is half the wavelength $\lambda$ of a microwave used and a width of several millimeters. Preferably, a matching slot 52 may be formed as shown in FIG. 2A, with its length measuring $\lambda/4$, for the purpose of obtaining matching. The diameter of the cylindrical conductor is not dimensionally limitative but may be determined to meet purposes. In the example of FIG. 2B, on the other hand, the antenna 50 is prepared by shaping an elongated conductor into a figure corresponding to the pattern of slots 51 in FIG. 2A. These examples of FIGS. 2A and 2B are substantially equivalent to a slot antenna of $\lambda/2$ length or an antenna constructed of a plurality of Lecher wires arranged to form, for example, a cylinder as shown in FIG. 2A and they are effective to generate the $TE_{01}$ mode of the microwave cavity.

Figure 3A:
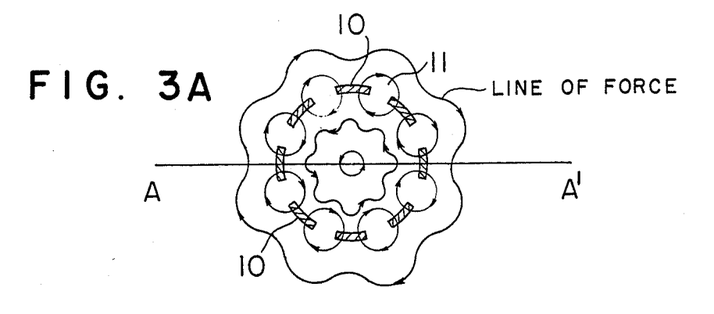
FIGS. 3A and 3B illustrate the microwave electric field distribution useful to explain the principle of the invention.
Figure 3B:
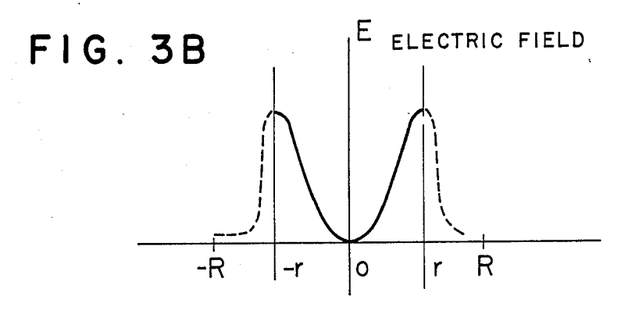

The electric field radiating from the microwave antenna 50 has a distribution in $TE_{01}$ mode as shown in FIGS. 3A and 3B. In particular, FIG. 3A illustrates a crosssection of line of electric force with arrow indicating the direction of electric field, and FIG. 3B graphically illustrates an electric field distribution in the radial direction. Dotted-line portions in FIG. 3B are representative of an electric field distribution obtained within a zone defined by R-r when a shielding box having a radius R larger than that r of a multiantenna 10 surrounds this antenna 10, where R-r is less than λ/2. As the number of slots 11 formed in the multi-antenna 10 increases, the circumferential contour of the electric field distribution illustrated in FIG. 3B approaches to a circle. The narrower the width of the slot 11, the stronger the electric field at the slot becomes and therefore the slot width is so selected as to meet purposes.

Through the use of this microwave power of $TE_{01}$ mode, doughnut type plasma resembling the RF inductively coupled plasma can be produced. In the doughnut type plasma, the electric field is tangential to concentric circles centered on the axis of the plasma and accordingly, when the density of electrons is decreased locally, the field strength is increased at that local area to increase the electron density, thereby producing stable plasma of good axis-symmetry. In addition, since the field distribution is raised at the circumferential contour as shown in FIG. 3B, the produced doughnut type plasma can have high temperatures at the circumferential contour. This ensures that sample particles can be introduced to the central part of the plasma easily and efficiently and besides the sample particles can be heated and atomized or ionized uniformly to improve various characteristics including detection sensitivity.

Figure 4:
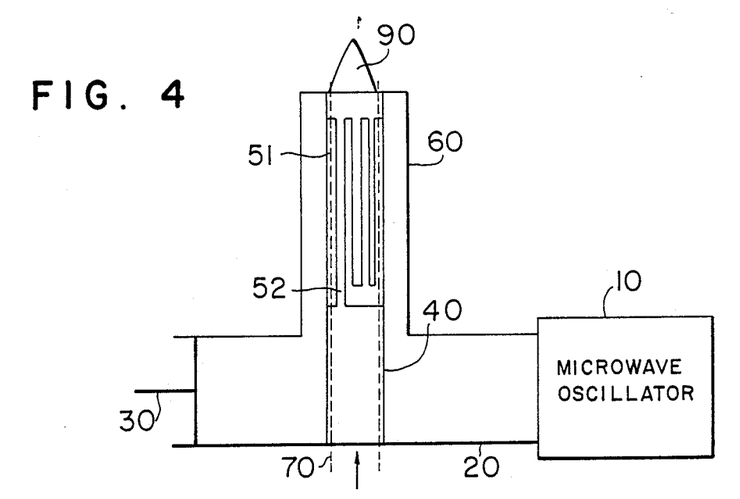
FIGS. 4 and 5 are schematic diagrams illustrating embodiments of an arrangement incorporating the antenna shown in FIG. 2A or 2B.

Referring to FIG. 4, an embodiment of an arrangement incorporating the antenna shown in FIG. 2A or 2B is schematically illustrated. Power from a microwave generator 10 is fed to an antenna 50 through a wave guide 20 and a mode transformer 40. Preferably, a variable tuner 30 may be provided in a manner shown in FIG. 4 so that the microwave power may be fed to the antenna 50 efficiently. Further, with a view of monitoring the power, a power meter comprised of, for example, a directional coupler may be provided in the wave guide 20. In addition, a shielding case 60, made of an electrically conductive material, may surround the antenna 50 to prevent power in the antenna 50 from leaking to the outside. Provided in the mode transformer 40 and antenna 50 is a discharge tube 70 made of an insulating material such as quartz glass. The discharge tube 70 has one end 80 through which samples at the center as well as a carrier gas and a cooling gas can be introduced. The other end of the discharge tube is opened to permit plasma 90 to spread forwardly. By adjusting the flow rate of the aforementioned gases and the level of the microwave power, the plasma 90 can be produced near the central part of the antenna 50.

Figure 5:
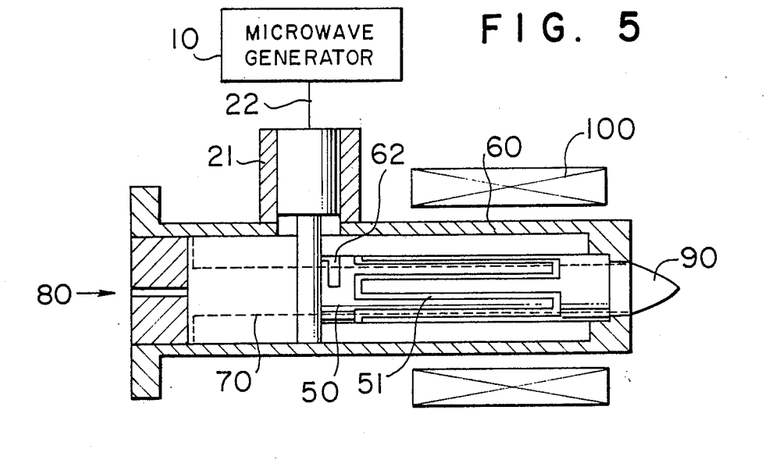

Referring to FIG. 5, another embodiment of the arrangement is illustrated wherein the microwave power is fed to the antenna 50 through the medium of a coaxial cable 22. In order to simplify plasma production, increase temperature and density of plasma and stabilize plasma, a magnet 100 such as coil or permanent magnet may preferably be provided to supply a magnetic field which may be of a multi-cusp or mirror type configuration.

Argon or helium is used as the carrier gas and the plasma is produced at atmospheric pressure or at a decreased pressure, that is, at a pressure ranging from $10^3$ Torr to $10^{-6}$ Torr.

Figure 6:
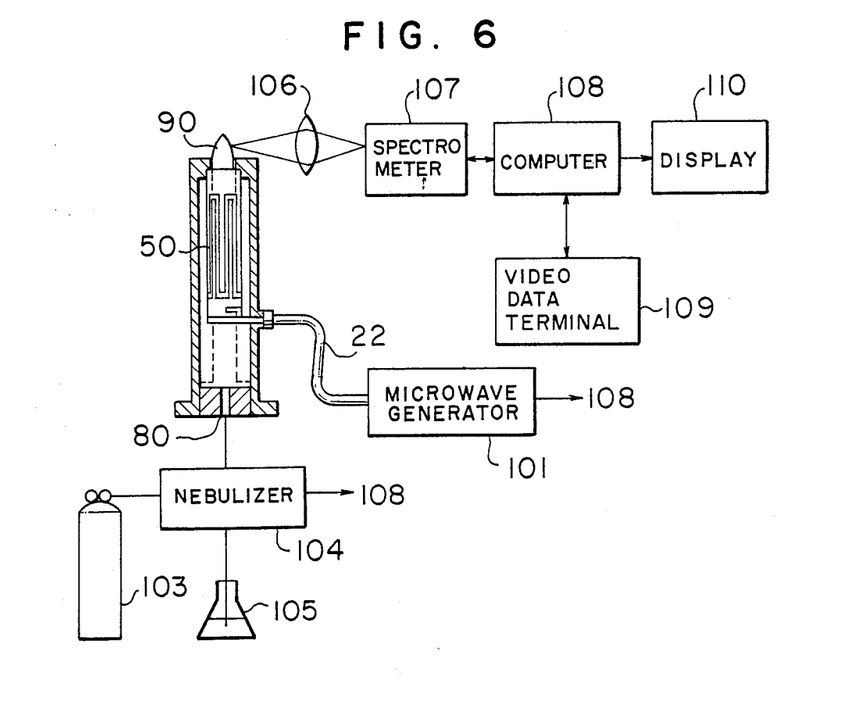
FIG. 6, FIGS. 7A and 7B, FIGS. 8A, 8B and 8C, and FIGS. 9A and 9B illustrate embodiments of the invention in which the invention is applied to different types of spectrometers.

In an embodiment of the invention as shown in FIG. 6, the antenna 50 is applied to an emission spectrometer.

Microwave power generated from a microwave generator 101 is fed to the antenna 50 by a coaxial cable 22. As described previously, an electric field of $TE_{01}$ mode is set up inside the antenna 50. In the microwave generator 101, reflected power is monitored and forward power is made to be constant under the control of a computer 108. An argon gas discharged from an argon gas bomb 103 is supplied to a nebulizer 104. A sample 105 is also supplied to the nebulizer 104 and nebulized thereby. The thus nebulized sample is fed, along with the argon gas, to the interior of the antenna 50 through the sample inlet port 80. Preferably, the above operation may be controlled automatically by means of the computer 108. The electric field set up in the antenna 50 causes breakdown of the argon gas and microwave discharge takes place at, for example atmospheric pressure. The set up electric field is stronger at the circumferential contour (near the antenna 50) and especially at this portion, plasma at high temperature is produced. This plasma is effective to cause ions of the introduced sample to move toward the center and to cause that sample to stay efficiently inside the plasma. As a result, the sample can be dissociated efficiently, the density of sample atoms or ions can be increased and the excitation temperature can be raised. Since the argon gas flows to the other end opposite to the sample inlet port 80, plasma 90 spreads outwards beyond the antenna 50. Light emission from the plasma 90 is focused on an inlet slit of a spectrometer 107 by means of a lens 106. When data representative of elements to be analyzed is inputted from a video data terminal 109, the spectrometer 107 sequentially selects wavelengths corresponding to the elements to be analyzed under the direction of signals from the computer 108 and measures intensity of emission at the selected wavelength to send the measurement results to the computer 108. The measurement results may be displayed on a display device 110 or stored under the control of the computer 108.

Although not shown in FIG. 6, a means of breakdown may be provided as necessary. The density of initial plasma produced by the means of breakdown is desired to be high. Preferably, spark discharge, arc discharge, glow discharge or RF monopole discharge may be used as the means of breakdown.

Alternatively, changing the gas pressure, for example, reducing the gas pressure only during breakdown may be used as the means of breakdown. In any case, preferably, the breakdown means may also be controlled by the computer 108.

Figure 7A:
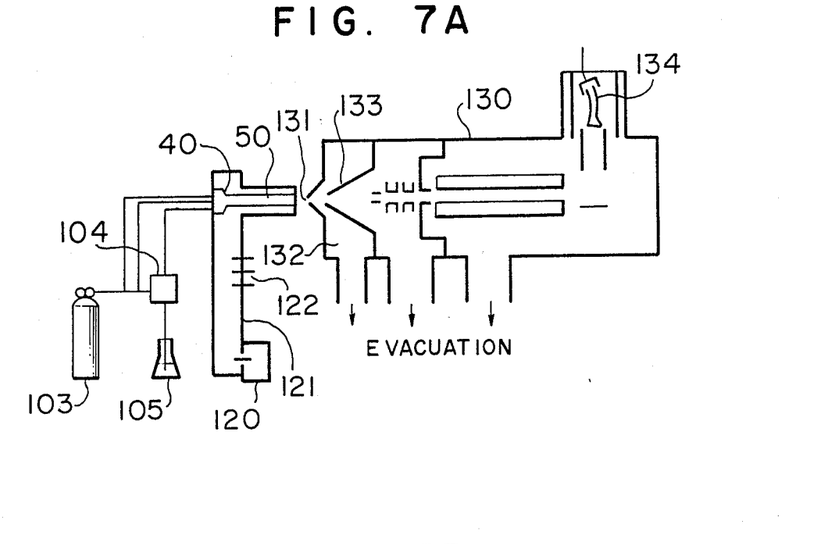
Figure 7B:
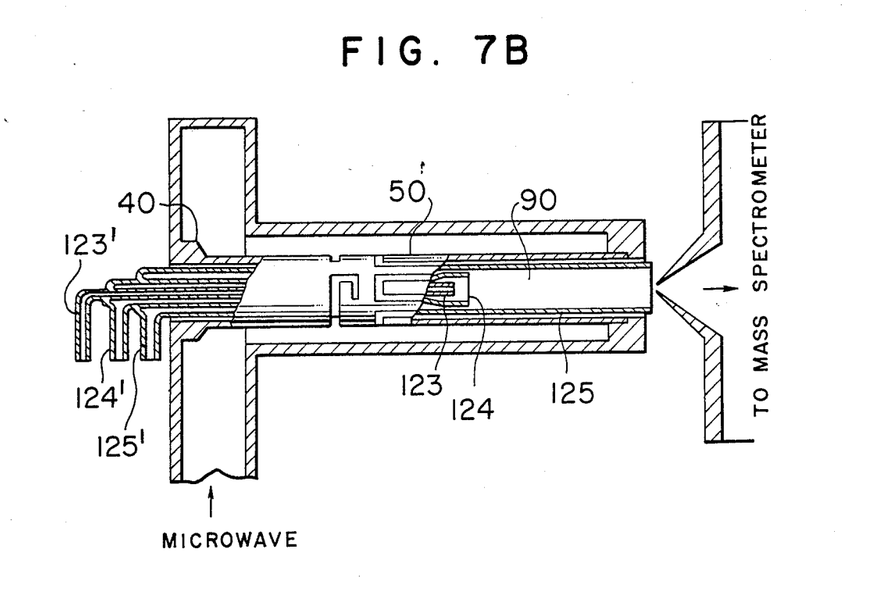

In another embodiment of the invention as shown in FIGS. 7A and 7B, the previously-described antenna 50 is applied to provide a plasma ion source in a mass spectrometer.

FIG. 7A schematically illustrates the overall construction of the mass spectrometer and FIG. 7B illustrates details of the antenna 50 and sample inlet port. Microwave power at 2450 MHz generated from a magnetron 120 is fed to the antenna 50 through a rectangular wave guide 121, a three-stab tuner 122 and a mode transformer 40. A triple tube made of quartz is disposed inside the antenna 50, as shown in FIG. 7B. Argon gas mainly used for production of plasma is supplied from an inlet 124′ into an intermediate quartz tube 124 inside the antenna 50. Plasma 90 is produced by the microwave power. This plasma 90 is a discharge at, for example atmospheric pressure and it can absorb the microwave power efficiently to be excited to high temperatures. Further, since the electric field is stronger at the circumferential contour, the temperature is higher there. In addition to the argon gas, a sample nebulized as in the case of the FIG. 6 embodiment is fed from an inlet 123' of an innermost quartz tube 123 and it reaches the center of the plasma 90. As described previously, the temperature of the plasma 90 is higher at the circumferential contour and the introduced sample stays efficiently inside the plasma, thereby permitting the sample to be ionized with high efficiency. Argon gas fed from an inlet 125' of an outermost quartz tube 125 is used for cooling. Ions in the plasma 90 are absorbed into a sub-vacuum chamber 132 through a sampling orifice 131 of a mass spectrometer 130. The sub-vacuum chamber 132 is evacuated to a pressure of the order of several Torr's by differential pumping. The ions then pass through a skimmer orifice 133 and subsequently undergo mass analysis so as to impinge upon an ion detector 134 for measurement.

Since in this embodiment the microwave power is supplied to the plasma through the use of the wave guide, the supply of a high level of power can be ensured easily. Consequently, the temperature rise of the plasma can be further enhanced, with the result that the number of molecular ions can be decreased and a mass spectrometer of less interference can be realized.

If a magnetic field is applied, as in the case of the FIG. 5 embodiment, to increase the ion density at the center, the sensitivity of the mass spectrometer can be further improved.

As the gas for plasma production, a rare gas, other than argon, or nitrogen can be used effectively and nitrogen is especially effective to provide a plasma ion source according to the invention.

Figure 8A:
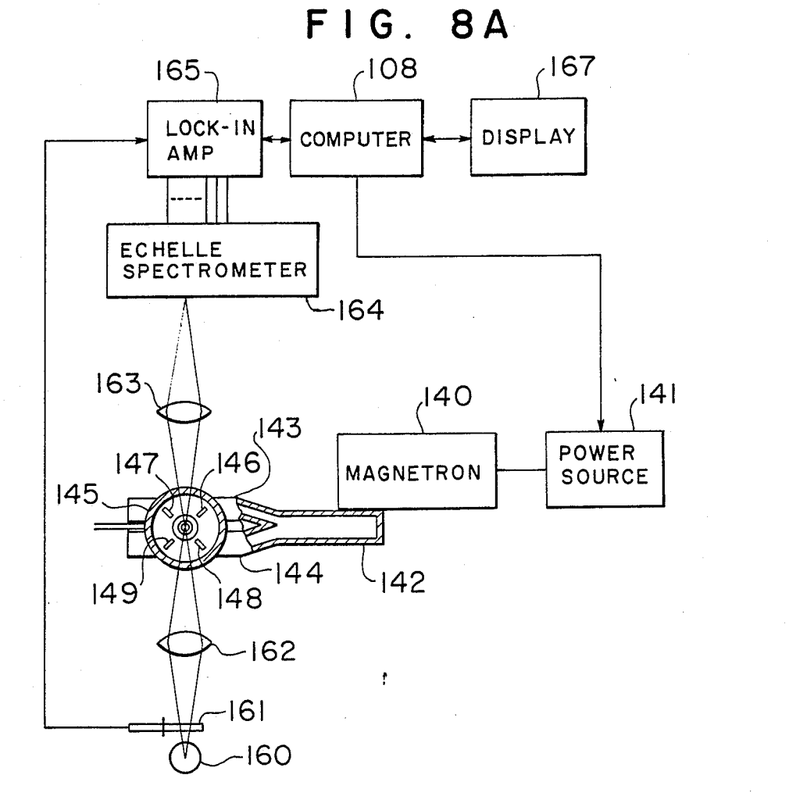
Figure 8B:
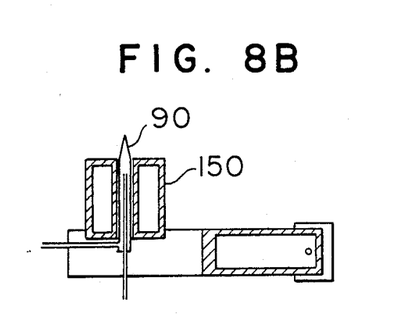
Figure 8C:
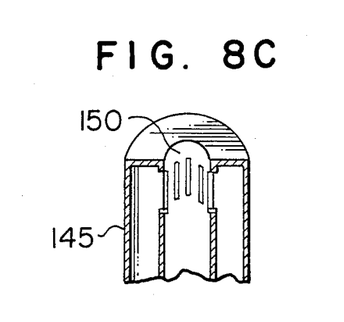
Figure 9A:
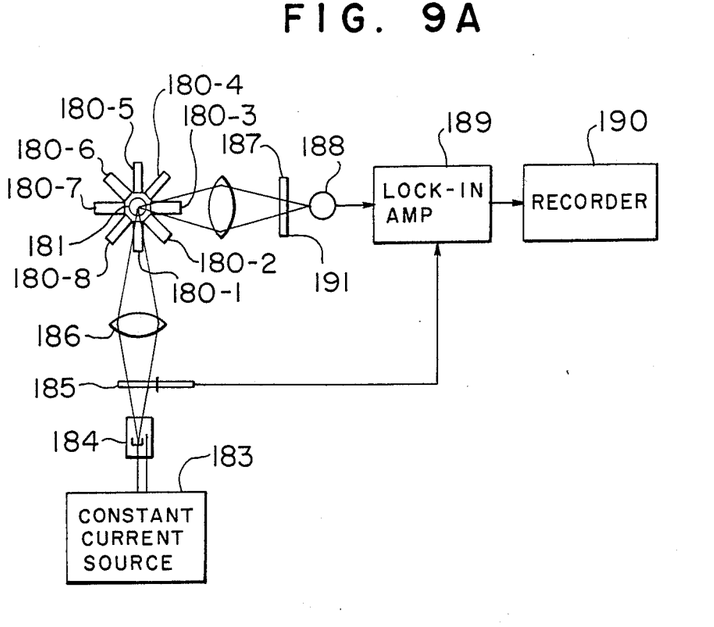
Figure 9B:
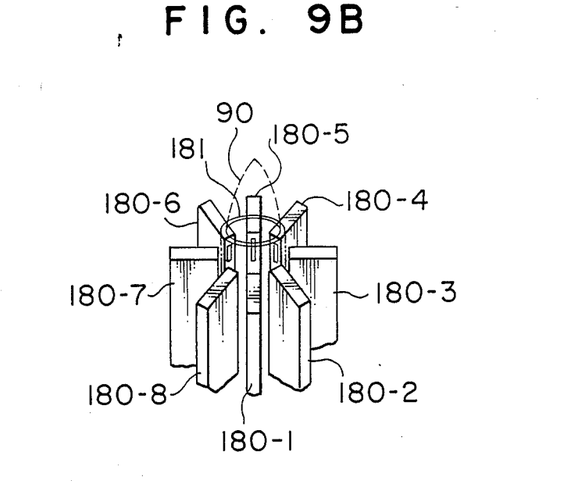

Referring now to FIGS. 8 and 9, further embodiments of the antenna for generation of the $TE_{01}$ mode according to the invention and their applications will be described.

In an embodiment of the invention as shown in FIGS. 8A, 8B and 8C, plasma produced in an electric field of $TE_{01}$ mode is used as an atomizer or an ion source in simultaneous multi-element atomic absorption spectroscopy. FIG. 8A schematically illustrates the overall construction of an arrangement for simultaneous multi-element atomic absorption spectroscopy, FIG. 8B details a plasma production portion in FIG. 8A, and FIG. 8C details an antenna structure for generation of the $TE_{01}$ mode.

A magnetron 140 is driven by a power source 141 to generate a microwave at 2450 MHz which is fed into a rectangular wave guide 142. The microwave is propagated in $TE_{01}$ mode (the fundamental mode of the rectangular wave guide) through the wave guide 142. As best seen in FIG. 8A, the rectangular wave guide 142 longitudinally extends to branch midway into rectangular wave guides 143 and 144. Accordingly, the microwave power is also halved and the halved power propagates into the rectangular wave guides 143 and 144, respectively. A cylindrical coaxial wave guide 145 is provided on the rectangular wave guides 143 and 144, having its bottom wall which is contiguous to the top surfaces of the wave guides 143 and 144 and which is formed with radial slits 146 and 147 running through the top of the wave guide 143 and radial slits 148 and 149 running through the top of the wave guide 144. The center-to-center distance between adjacent slits is half the guide wavelength $\lambda_g$ of the rectangular wave guide. The microwave power propagates through these slits to excite the $TE_{01}$ mode inside the cylindrical coaxial wave guide 145. The $TE_{01}$ mode inside the cylindrical coaxial wave guide is concomitant with a surface current which is orthogonal to the wave guide axis. Turning to FIG. 8C, the cylindrical coaxial wave guide 145 has its tip portion where the inner and outer conductors of the coaxial wave guide 145 are electrically jointed together by an annular end plate and a plurality of axial slits 150 are formed in the inner conductor, having the center which is distant from the end plate by about $\frac{1}{4}$ of the guide wavelength. These slits 150 cut the surface current inside the wave guide to act as a slot antenna which generates an electric field of $TE_{01}$ mode in the interior of the inner conductor.

An argon gas necessary for production of plasma and an argon gas containing a nebulized sample are supplied through a bottom opening of the coaxial wave guide 145 to the interior of the inner conductor and they coact with the electric field of $TE_{01}$ mode taking place in front of the slits 150 to produce plasma 90.

A light beam emitted from a continuous spectrum light source 160 such as xenon lamp is modulated by a chopper 161 and thereafter focused on the plasma 90 by means of a lens 162. Light of a wavelength corresponding to a resonance line of atom or ion is absorbed in the plasma 90. A light beam of the wavelength subject to absorption is focused on an inlet slit of an echelle spectrometer 164 by means of a lens 163. The absorbed light beam is subjected to order separation in the echelle spectrometer 164. Outlet slits of the spectrometer 164 are located at positions corresponding to wavelengths of resonance lines of individual elements, and photodetectors are provided at the back of the photodetectors. Output signals of the photodetectors are sent to a lock-in amplifier 165 at which they are amplified in synchronism with signals from the chopper 161. The output signals of the lock-in amplifier are sequentially fetched by a computer 108 and after subjected to necessary processing at the computer, they are displayed on a display device 167. The computer 108 is also used for automatic control of the overall arrangement of FIG. 8A.

In this embodiment, a high level of microwave power can be supplied easily to the plasma through the use of the wave guide. The length of each slit 150 approximating the half wavelength is optimal but this length can be shorter, as necessary. With shorter length, microwave power can be supplied concentratedly to a narrower area.

In a further embodiment of the invention as shown in FIGS. 9A and 9B, plasma produced in an electric field of $TE_{01}$ mode is used as an atomizer or an ion source in an atomic fluorescent spectrometer. FIG. 9A schematically illustrates the overall construction of the atomic fluorescent spectrometer and FIG. 9B details a plasma production portion having an antenna structure for generation of the $TE_{01}$ mode.

Denoted by 180-1, 180-2, ..., 180-8 are rectangular wave guides. These wave guides are arranged on a circle so that the inner short side of one wave guide diametrally opposes the inner short side of another wave guide. As shown in FIG. 9B, each rectangular wave guide is closed, at one end, by an end plate and has a slit formed in the inner short side at a position which is distant from the one end by about $\frac{1}{4}$ of the guide wavelength. When the $TE_{01}$ mode standing for the fundamental mode of the rectangular wave guide is excited therein, the slits cut the surface current to act as a slot antenna. Electric fields from the eight slits are superimposed on each other to generate an electric field of $TE_{01}$ mode in a space surrounded by the rectangular wave guides. In this case, the excitation at each slit must be in phase. To this end, it is preferable that the excitation be obtained in a single wave guide by using a single microwave source, and that this excitation is divided at a division point which is equidistant from each slit.

A quartz tube 181 is disposed in the space surrounded by the rectangular wave guides and an argon gas containing a nebulized sample flows through the quartz tube 181 Plasma 90 is produced by the electric field of $TE_{01}$ mode taking place in front of the slits.

A light beam emitted from a hollow cathode lamp 184 turned on by being fed from a constant current source 183 passes through a chopper 185 and is then focused on the plasma 90 by means of a lens 186. When there exist in the plasma 90 atoms of an element whose wavelength of resonance line is identical to the wavelength of light emitted from the hollow cathode lamp 184, these atoms absorb the light beam from the hollow cathode lamp and fluorescence. The fluorescence, after passing through a filter 191, is focused on a photodetector 188 by means of a lens 187. An output signal of the photodetector 188 is sent to a lock-in amplifier 189 at which it is amplified in synchronism with a signal from the chopper 185. An output signal of the amplifier is sent to a recorder 190 so as to be recorded therein.

Advantageously, in the present embodiment, the slits for generation of the $TE_{01}$ mode can be provided separately. Thus, even if the rectangular wave guides 180-1 and 180-3 on the optical path, for example, are omitted, the plasma can be produced in front of the slits without causing the electric field to deviate greatly from the $TE_{01}$ mode. Although the invention has been described by referring to preferred embodiments thereof, the foregoing embodiments are not limitative and various alternations, modifications and combinations may obviously be realizable.

According to the invention, the microwave power of $TE_{01}$ mode is used to attain the following effects. Firstly, the prior art RF inductively coupled plasma spectrometer using RF power at about 27 MHz is disadvantageous in that the RF power supply used for plasma production has so large a capacity as amounting to 1 KW to 2 KW and is complicated in construction, resulting in extreme expensiveness and that impedance matching between the RF power supply and load is delicate and the matchable range is narrow, but the use of microwave can eliminate these disadvantages relatively easily. For example, as the microwave source, the magnetron can be used which can be supplied relatively inexpensively through mass production. Further, the impedance matching can be achieved easily for the overall load range by using, for example, the three-stab tuner.

Secondly, through the use of the $TE_{01}$ mode, the doughnut type plasma can be produced easily and efficiently to ensure that the samples can be introduced efficiently and can be heated and ionized uniformly, thereby improving the detection sensitivity doubly or more.

We claim:

1. A plasma trace element spectrometer comprising:
    microwave generation means for generating microwave power;
    microwave feed means for guiding and transforming the generated microwave power into microwave power of $TE_{01}$ mode and supplying the microwave power of $TE_{01}$ mode;
    plasma production means having, at one end, an introduction port for a carrier gas and a sample and at the other end an opening and being cooperative with the supplied microwave power of $TE_{01}$ mode to produce plasma of the carrier gas and sample introduced through said introduction port; and
    spectrometer means for analyzing constituent elements of said sample by measuring the produced plasma by way of said opening.

2. A plasma trace element spectrometer according to claim 1 wherein said microwave feed means comprises a microwave antenna.

3. A plasma trace element spectrometer according to claim 1 wherein said plasma is produced at atmospheric pressure.

4. A plasma trace element spectrometer according to claim 2 wherein said plasma is produced at atmospheric pressure.

5. A plasma trace element spectrometer according to claim 1 wherein said plasma generation means comprises magnetic field applying means.

6. A plasma trace element spectrometer according to claim 2 wherein said plasma generation means comprises magnetic field applying means.

* * * * *